(12) United States Patent
Park et al.

(10) Patent No.: US 8,383,379 B2
(45) Date of Patent: Feb. 26, 2013

(54) COPOLYMER COMPRISING 4-HYDROXYBUTYRATE UNIT AND LACTATE UNIT AND ITS MANUFACTURING METHOD

(75) Inventors: Si-Jae Park, Daejeon (KR); Taek-Ho Yang, Daejeon (KR); Hye-Ok Kang, Daejeon (KR); Sang-Hyun Lee, Daejeon (KR); Eun-Jeong Lee, Daejeon (KR); Tae-Wan Kim, Daejeon (KR); Sang-Yup Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 693 days.

(21) Appl. No.: 12/312,635

(22) PCT Filed: Nov. 21, 2007

(86) PCT No.: PCT/KR2007/005852
§ 371 (c)(1),
(2), (4) Date: Nov. 20, 2009

(87) PCT Pub. No.: WO2008/062995
PCT Pub. Date: May 29, 2008

(65) Prior Publication Data
US 2010/0222545 A1    Sep. 2, 2010

(30) Foreign Application Priority Data

Nov. 21, 2006  (KR) .................. 10-2006-0115158
Nov. 21, 2006  (KR) .................. 10-2006-0115159
Nov. 21, 2006  (KR) .................. 10-2006-0115160
Nov. 21, 2006  (KR) .................. 10-2006-0115161

(51) Int. Cl.
C12N 9/00      (2006.01)
C07H 21/04     (2006.01)
A01N 63/00     (2006.01)

(52) U.S. Cl. ........ 435/183; 424/93.2; 424/93.4; 435/41; 435/139; 435/410; 435/419; 536/23.2; 536/23.7

(58) Field of Classification Search ........... 424/93.2, 424/93.4; 435/41, 139, 183, 410, 419; 536/23.2, 536/23.7
See application file for complete search history.

Primary Examiner — Rodney P. Swartz
(74) Attorney, Agent, or Firm — McKenna Long & Aldridge, LLP

(57) ABSTRACT

The present invention relates to a copolymer comprising 4-hydroxybutyrate monomer unit and lactate monomer unit, a copolymer 4-hydroxybutyrate monomer unit, lactate monomer unit and 3-hydroxyalkanoate, or their preparing method. More specifically, the present invention relates to a method for preparing a copolymer comprising lactate monomer; 4-hydroxybutyrate monomer; and optionally 3-hydroxyalkanoate, wherein the method comprises culturing a cell or plant comprising the gene of enzyme converting lactate and 3-hydroxyalkanoate into lactyl-CoA and 3-hydroxyalkanoyl-CoA, respectively, phosphotransbutylase gene, butyrate kinase gene and polyhydroxyalkanoate synthase gene together, and the copolymer made by the method. The copolymer of the present invention is a biodegradable polymer being able to be usefully used instead of conventional synthetic plastic, and the copolymer can be used for medical use.

12 Claims, 6 Drawing Sheets

```
                        SEQUENCE LISTING

<160> NUMBER OF SEQ ID NOS: 46

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1
ggaattcatg agaaaggttc ccattattac cgcagatga                          39

<210> SEQ ID NO 2
<211> LENGTH: 46
<212> TYPE: DNA
<213> ORGANISM: Artificial Sequence
<220> FEATURE:
<223> OTHER INFORMATION: primer

<400> SEQUENCE: 2
gctctagatt aggacttcat ttccttcaga cccattaagc cttctg                  46

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
aggcctgcag gcggataaca atttcacaca gg                                 32

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
gcccatatgt ctagattagg acttcatttc c                                  31

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
gagagacaat caaatcatga gtaacaagag taacg                              35

<210> SEQ ID NO 6
<211> LENGTH: 33
<212> TYPE: DNA
<213> ORGANISM: Artificial Sequence
```

<220> FEATURE:
<223> OTHER INFORMATION: primer

<400> SEQUENCE: 6
cactcatgca agcgtcaccg ttcgtgcacg tac                                33

<210> SEQ ID NO 7
<211> LENGTH: 1677
<212> TYPE: DNA
<213> ORGANISM: Pseudomonas sp. 6-19 (KCTC11027BP)

<400> SEQUENCE: 7
atgagtaaca agagtaacga tgagttgaag tatcaagcct ctgaaaacac cttggggctt     60
aatcctgtcg ttgggctgcg tggaaaggat ctactggctt ctgctcgaat ggtgcttagg    120
caggccatca agcaaccggt gcacagcgtc aaacatgtcg cgcactttgg tcttgaactc    180
aagaacgtac tgctgggtaa atccgggctg caaccgacca gcgatgaccg tcgcttcgcc    240
gatccggcct ggagccagaa cccgctctat aaacgttatt tgcaaaccta cctggcgtgg    300
cgcaaggaac tccacgactg gatcgatgaa agtaacctcg cccccaagga tgtggcgcgt    360
gggcacttcg tgatcaacct catgaccgaa gcgatggcgc cgaccaacac gcggccaac    420 ccggcggcag tcaaacgctt ttttgaaacc ggtggcaaaa gcctgctcga cggcctctcg    480
cacctggcca aggatctggt acacaacggc ggcatgccga ccaggtcaa catgggtgca    540 ttcgaggtcg gcaagagcct gggcgtgacc gaaggcgcgg tggtgtttcg caacgatgtg    600
ctggaactga tccagtacaa gccgaccacc gagcaggtat acgaacgccc gctgctggtg    660
gtgccgccgc agatcaacaa gttctacgtt ttcgacctga gcccggacaa gagcctggcg    720
cggttctgcc tgcgcaacaa cgtgcaaacg ttcatcgtca gctggcgaaa tcccaccaag    780
gaacagcgag agtggggcct gtcgacctac atcgaagccc tcaaggaagc ggttgacgtc    840
gttaccgcga tcaccggcag caaagacgtg aacatgctcg gggcctgctc cggcggcatc    900
acttgcactg cgctgctggg ccattacgcg gcgattggcg aaaacaaggt caacgccctg    960
accttgctgg tgagcgtgct tgataccacc ctcgacagcg acgtcgccct gttcgtcaat   1020
gaacagaccc ttgaagccgc caagcgccac tcgtaccagg ccggcgtact ggaaggccgc   1080
gacatggcga aggtcttcgc ctggatgcgc cccaacgatc tgatctggaa ctactgggtc   1140
aacaattacc tgctaggcaa cgaaccgccg gtgttcgaca tcctgttctg gaacaacgac   1200
accacacggt tgcccgcggc gttccacggc gacctgatcg aactgttcaa aaataaccca   1260
ctgattcgcc cgaatgcact ggaagtgtgc ggcaccccca tcgacctcaa gcaggtgacg   1320
gccgacatct tttccctggc cggcaccaac gaccacatca ccccgtggaa gtcctgctac   1380
aagtcggcgc aactgtttgg cggcaacgtt gaattcgtgc tgtcgagcag cgggcatatc   1440
cagagcatcc tgaacccgcc gggcaatccg aaatcgcgct acatgaccag caccgaagtg   1500
gcggaaaatg ccgatgaatg gcaagcgaat gccaccaagc atacagattc ctggtggctg   1560
cactggcagg cctggcaggc ccaacgctcg ggcgagctga aaaagtcccc gacaaaactg   1620
ggcagcaagg cgtatccggc aggtgaagcg gcgccaggca cgtacgtgca cgaacgg      1677

<210> SEQ ID NO 8
<211> LENGTH: 559
<212> TYPE: PRT
<213> ORGANISM: Pseudomonas sp. 6-19 (KCTC11027BP)

<400> SEQUENCE: 8

Met Ser Asn Lys Ser Asn Asp Glu Leu Lys Tyr Gln Ala Ser Glu Asn

```
  1               5                   10                  15
Thr Leu Gly Leu Asn Pro Val Val Gly Leu Arg Gly Lys Asp Leu Leu
                 20                  25                  30

Ala Ser Ala Arg Met Val Leu Arg Gln Ala Ile Lys Gln Pro Val His
         35                  40                  45

Ser Val Lys His Val Ala His Phe Gly Leu Glu Leu Lys Asn Val Leu
     50                  55                  60

Leu Gly Lys Ser Gly Leu Gln Pro Thr Ser Asp Arg Arg Phe Ala
 65              70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Asp Trp Ile Asp Glu Ser Asn
             100                 105                 110

Leu Ala Pro Lys Asp Val Ala Arg Gly His Phe Val Ile Asn Leu Met
         115                 120                 125

Thr Glu Ala Met Ala Pro Thr Asn Thr Ala Ala Asn Pro Ala Ala Val
     130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
             165                 170                 175

Asn Met Gly Ala Phe Glu Val Gly Lys Ser Leu Gly Val Thr Glu Gly
         180                 185                 190

Ala Val Val Phe Arg Asn Asp Val Leu Glu Leu Ile Gln Tyr Lys Pro
     195                 200                 205

Thr Thr Glu Gln Val Tyr Glu Arg Pro Leu Leu Val Val Pro Pro Gln
210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
             245                 250                 255

Asn Pro Thr Lys Glu Gln Arg Glu Trp Gly Leu Ser Thr Tyr Ile Glu
         260                 265                 270

Ala Leu Lys Glu Ala Val Asp Val Thr Ala Ile Thr Gly Ser Lys
     275                 280                 285

Asp Val Asn Met Leu Gly Ala Cys Ser Gly Gly Ile Thr Cys Thr Ala
     290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
             325                 330                 335

Leu Phe Val Asn Glu Gln Thr Leu Glu Ala Ala Lys Arg His Ser Tyr
         340                 345                 350

Gln Ala Gly Val Leu Glu Gly Arg Asp Met Ala Lys Val Phe Ala Trp
     355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
             405                 410                 415

Lys Asn Asn Pro Leu Ile Arg Pro Asn Ala Leu Glu Val Cys Gly Thr
         420                 425                 430
```

```
Pro Ile Asp Leu Lys Gln Val Thr Ala Asp Ile Phe Ser Leu Ala Gly
    435                 440                 445

Thr Asn Asp His Ile Thr Pro Trp Lys Ser Cys Tyr Lys Ser Ala Gln
450                 455                 460

Leu Phe Gly Gly Asn Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
            500                 505                 510

Lys His Thr Asp Ser Trp Trp Leu His Trp Gln Ala Trp Gln Ala Gln
515                 520                 525

Arg Ser Gly Glu Leu Lys Lys Ser Pro Thr Lys Leu Gly Ser Lys Ala
    530                 535                 540

Tyr Pro Ala Gly Glu Ala Ala Pro Gly Thr Tyr Val His Glu Arg
545                 550                 555
```

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
atgcccggag ccggttcgaa                                            20

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
cgttactctt gttactcatg atttgattgt ctctc                           35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
gagagacaat caaatcatga gtaacaagag taacg                           35

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
cactcatgca agcgtcaccg ttcgtgcacg tac                             33

<210> SEQ ID NO 13
<211> LENGTH: 33
<212> TYPE: DNA
<213> ORGANISM: Artificial Sequence
<220> FEATURE:
<223> OTHER INFORMATION: primer

```
<400> SEQUENCE: 13
gtacgtgcac gaacggtgac gcttgcatga gtg                              33

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aacgggaggg aacctgcagg                                             20

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
atcaacctca tgaccgatgc gatggcgccg acc                              33

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
ggtcggcgcc atcgcatcgg tcatgaggtt gat                              33

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
ctgaccttgc tggtgaccgt gcttgatacc acc                              33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
ggtggtatca agcacggtca ccagcaaggt cag                              33

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
cgagcagcgg gcatatcatg agcatcctga acccgc                           36

<210> SEQ ID NO 20
<211> LENGTH: 36
<212> TYPE: DNA
```

<213> ORGANISM: Artificial Sequence
<220> FEATURE:
<223> OTHER INFORMATION: primer

<400> SEQUENCE: 20
gcgggttcag gatgctcatg atatgcccgc tgctcg          36

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
ggaaatccat atgacgatgt tctcgctcat ggcg          34

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
ggaaatccat atgatccagg gccactatct ccaactg          37

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
ggcagagaga caatcaaatc atgattaaga gttttaatg          39

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
ggaattccat atgttatttg tattccttag cttttcttc tcc          43

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gggcagatgt gccggcagac          20

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gatttgattg tctctctgcc g          21

```
<210> SEQ ID NO 27
<211> LENGTH: 906
<212> TYPE: DNA
<213> ORGANISM: Unknown
<220> FEATURE:
<223> OTHER INFORMATION: Ptb-coding gene

<400> SEQUENCE: 27
gtgattaaga gttttaatga aattatcatg aaggtaaaga gcaaagaaat gaaaaaagtt      60
gctgttgctg tagcacaaga cgagccagta cttgaagcag taagagatgc taagaaaaat     120
ggtattgcag atgctattct tgttggagac catgacgaaa tcgtgtcaat cgcgcttaaa     180
ataggaatgg atgtaaatga ttttgaaata gtaaacgagc ctaacgttaa gaaagctgct     240
ttaaaggcag tagagcttgt atcaactgga aaagctgata tggtaatgaa gggacttgta     300
aatacagcaa ctttcttaag atctgtatta aacaagaag ttggacttag aacaggaaaa      360
actatgtctc acgttgcagt attgaaact gagaaatttg atagactatt atttttaaca      420
gatgttgctt tcaatactta tcctgaatta aaggaaaaaa ttgatatagt aaacaattca     480
gttaaggttg cacatgcaat aggaattgaa aatccaaagg ttgctccaat ttgtgcagtt     540
gaggttataa accctaaaat gccatcaaca cttgatgcag caatgctttc aaaaatgagt     600
gacagaggac aaattaaagg ttgtgtagtt gacggaccct tagcacttga tatagcttta     660
tcagaagaag cagcacatca taagggagta acaggagaag ttgctggaaa agctgatatc     720
ttcttaatgc caaacataga aacaggaaat gtaatgtata agactttaac atatacaact     780
gattcaaaaa atggaggaat cttagttgga acttctgcac cagttgtttt aacttcaaga     840
gctgacagcc atgaaacaaa aatgaactct atagcacttg cagctttagt tgcaggcaat     900
aaataa                                                                906

<210> SEQ ID NO 28
<211> LENGTH: 1068
<212> TYPE: DNA
<213> ORGANISM: Unknown
<220> FEATURE:
<223> OTHER INFORMATION: Buk-coding gene

<400> SEQUENCE: 28
atgtatagat tactaataat caatcctggc tcgacctcaa ctaaaattgg tatttatgac      60
gatgaaaaag agatatttga gaagacttta agacattcag ctgaagagat agaaaaatat     120
aacactatat tgatcaatt tcaattcaga aagaatgtaa ttttagatgc gttaaaagaa      180
gcaaacatag aagtaagttc tttaaatgct gtagttggaa gaggcggact cttaaagcca     240
atagtaagtg gaacttatgc agtaaatcaa aaaatgcttg aagaccttaa gtaggagtt     300 caaggtcagc atgcgtcaaa tcttggtgga attattgcaa atgaaatagc aaaagaaata     360
aatgttccag catacatagt tgatccagtt gttgtggatg agcttgatga agtttcaaga     420
atatcaggaa tggctgacat tccaagaaaa agtatattcc atgcattaaa tcaaaaagca     480
gttgctagaa gatatgcaaa agaagttgga aaaaaatacg aagatcttaa tttaatcgta     540
gtccacatgg gtggaggtac ttcagtaggt actcataaag atggtagagt aatagaagtt     600
aataatacac ttgatggaga aggtccattc tcaccagaaa gaagtggtgg agttccaata     660
ggagatcttg taagattgtg cttcagcaac aaatatactt atgaagaagt aatgaaaaag     720
ataaacggca aggcggagt tgttagttac ttaaatacta tcgattttaa ggctgtagtt     780
gataaagctc ttgaaggaga taagaaatgt gcacttatat atgaagcttt cacattccag     840
```

```
gtagcaaaag agataggaaa atgttcaacc gttttaaaag gaaatgtaga tgcaataatc    900
ttaacaggcg gaattgcgta caacgagcat gtatgtaatg ccatagagga tagagtaaaa    960
ttcatagcac ctgtagttag atatggtgga gaagatgaac ttcttgcact tgcagaaggt   1020
ggacttagag ttttaagagg agaagaaaaa gctaaggaat acaaataa                1068
```

<210> SEQ ID NO 29
<211> LENGTH: 1572
<212> TYPE: DNA
<213> ORGANISM: Clostridium propionicum
<220> FEATURE:
<223> OTHER INFORMATION: Propionyl-CoA transferase

<400> SEQUENCE: 29

```
atgagaaagg ttcccattat taccgcagat gaggctgcaa agcttattaa agacggtgat     60
acagttacaa caagtggttt cgttggaaat gcaatccctg aggctcttga tagagctgta    120
gaaaaaagat tcttagaaac aggcgaaccc aaaaacatta cctatgttta ttgtggttct    180
caaggtaaca gagacggaag aggtgctgag cactttgctc atgaaggcct tttaaaacgt    240
tacatcgctg gtcactgggc tacagttcct gctttgggta aaatggctat ggaaaataaa    300
atggaagcat ataatgtatc tcagggtgca ttgtgtcatt tgttccgtga tatagcttct    360
cataagccag gcgtatttac aaaggtaggt atcggtactt tcattgaccc cagaaatggc    420
ggcggtaaag taatgatat taccaaagaa gatattgttg aattggtaga gattaagggt    480
caggaatatt tattctaccc tgcttttcct attcatgtag ctcttattcg tggtacttac    540
gctgatgaaa gcggaaatat cacatttgag aaagaagttg ctcctctgga aggaacttca    600
gtatgccagg ctgttaaaaa cagtggcggt atcgttgtag ttcaggttga agagtagta    660 aaagctggta ctcttgaccc tcgtcatgta aaagttccag gaattatgt tgactatgtt    720 gttgttgctg acccagaaga tcatcagcaa tctttagatt gtgaatatga tcctgcatta    780
tcaggcgagc atagaagacc tgaagttgtt ggagaaccac ttcctttgag tgcaaagaaa    840
gttattggtc gtcgtggtgc cattgaatta gaaaagatg ttgctgtaaa tttaggtgtt    900
ggtgcgcctg aatatgtagc aagtgttgct gatgaagaag gtatcgttga ttttatgact    960
ttaactgctg aaagtggtgc tattggtggt gttcctgctg gtggcgttcg ctttggtgct   1020
tcttataatg cggatgcatt gatcgatcaa ggttatcaat cgattactaa tgatggcggc   1080
ggcttagacc tttgctattt aggcttagct gaatgcgatg aaaaaggcaa tatcaacgtt   1140
tcaagatttg gccctcgtat cgctggttgt ggtggtttca tcaacattac acagaataca   1200
cctaaggtat tcttctgtgg tactttcaca gcaggtggct aaaggttaa aattgaagat   1260 ggcaaggtta ttattgttca agaaggcaag cagaaaaaat tcttgaaagc tgttgagcag   1320
attacattca atggtgacgt tgcacttgct aataagcaac aagtaactta tattacagaa   1380
agatgcgtat tcctttgaa ggaagatggt ttgcacttat ctgaaattgc acctggtatt   1440
gatttgcaga cacagattct tgacgttatg gatttgcac ctattattga cagagatgca   1500
aacggccaaa tcaaattgat ggacgctgct ttgtttgcag aaggcttaat gggtctgaag   1560
gaaatgaagt cc                                                       1572
```

<210> SEQ ID NO 30
<211> LENGTH: 1290
<212> TYPE: DNA
<213> ORGANISM: Unknown
<220> FEATURE:
<223> OTHER INFORMATION: 4HB-CoA transferase-coding gene

```
<400> SEQUENCE: 30
atggagtggg aagagatata taaagagaaa ctggtaactg cagaaaaagc tgtttcaaaa     60
atagaaaacc atagcagggt agtttttgca catgcagtag gagaacccgt agatttagta    120
aatgcactag ttaaaaataa ggataattat ataggactag aaatagttca catggtagct    180
atgggcaaag gtgtatatac aaaagagggt atgcaaagac attttagaca taatgctttg    240
tttgtaggcg gatctactag agatgcagta aattcaggaa gagcagttta tacaccttgt    300
tttttctatg aagtgccaag tttgtttaaa gaaaaacgtt tgcctgtaga tgtagcactt    360
attcaggtaa gtgagccaga taatatggc tactgcagtt ttggagtttc caatgactat    420
accaagccag cagcagaaag tgctaagctt gtaattgcag aagtgaataa aaacatgcca    480
agaactcttg gagattcttt tatacatgta tcagatattg attatatagt ggaagcttca    540
cacccattgt tagaattgca gcctcctaaa ttgggagatg tagaaaaagc cataggagaa    600
aactgtgcat cttttaattga agatggagct actcttcagc ttggaatagg tgctatacca    660
gatgcggtac ttttattctt aaagaacaaa aagaatttag gaatacattc tgagatgata    720
tcagatggtg tgatggaact ggtgaaggca ggggttatca ataacaagaa aaagaccctc    780
catccaggca aaatagttgt aacattttta atgggaacaa aaaaattata tgattttgta    840
aacaataatc caatggtaga aacttattct gtagattatg taaataatcc actggtaatt    900
atgaaaaatg acaatatggt ttcaataaat tcttgtgttc aagtagactt aatgggacaa    960
gtatgttctg aaagtatagg attgaaacag ataagtggag tggggaggcca ggtagatttt   1020
attagaggag ctaatctatc aaagggtgga aaggctatta tagctatacc ttccacagct   1080
ggaaaaggaa aagtttcaag aataactcca cttctagata ctggtgctgc agttacaact   1140
tctagaaatg aagtagatta tgtagttact gaatatggtg ttgctcatct taagggcaaa   1200
actttaagaa atagggcaag agctctaata aatatcgctc atccaaaatt cagagaatca   1260
ttaatgaatg aattttaaaaa gagattttag                                    1290

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gaattcgtgc tgtcgagccg cgggcatatc                                      30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gatatgcccg cggctcgaca gcacgaattc                                      30

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
```

```
gaattcgtgc tgtcgagcca tgggcatatc                                          30
```

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34

```
gatatgccca tggctcgaca gcacgaattc                                          30
```

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35

```
gaattcgtgc tgtcgagctt tgggcatatc                                          30
```

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36

```
gatatgccca aagctcgaca gcacgaattc                                          30
```

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37

```
gaattcgtgc tgtcgagcta tgggcatatc                                          30
```

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38

```
gatatgccca tagctcgaca gcacgaattc                                          30
```

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39

```
gaattcgtgc tgtcgagcgg cgggcatatc                                          30
```

<210> SEQ ID NO 40
<211> LENGTH: 30
<212> TYPE: DNA
<213> ORGANISM: Artificial Sequence
<220> FEATURE:

<223> OTHER INFORMATION: Primer

<400> SEQUENCE: 40
gatatgcccg ccgctcgaca gcacgaattc                              30

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
gggcatatca aaagcatcct gaacccgc                                28

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
gcgggttcag gatgcttttg atatgccc                                28

<210> SEQ ID NO 43
<211> LENGTH: 28
<212> TYPE: DNA
<213> ORGANISM: Artificial Sequence
<220> FEATURE:
<223> OTHER INFORMATION: Primer

<400> SEQUENCE: 43
gggcatatca tgagcatcct gaacccgc                                28

<210> SEQ ID NO 44
<211> LENGTH: 28
<212> TYPE: DNA
<213> ORGANISM: Artificial Sequence
<220> FEATURE:
<223> OTHER INFORMATION: Primer

<400> SEQUENCE: 44
gcgggttcag gatgctcatg atatgccc                                28

<210> SEQ ID NO 45
<211> LENGTH: 28
<212> TYPE: DNA
<213> ORGANISM: Artificial Sequence
<220> FEATURE:
<223> OTHER INFORMATION: Primer

<400> SEQUENCE: 45
gggcatatcc gcagcatcct gaacccgc                                28

<210> SEQ ID NO 46
<211> LENGTH: 28
<212> TYPE: DNA
<213> ORGANISM: Artificial Sequence
<220> FEATURE:
<223> OTHER INFORMATION: Primer

<400> SEQUENCE: 46
gcgggttcag gatgctgcgg atatgccc                                28

COPOLYMER COMPRISING 4-HYDROXYBUTYRATE UNIT AND LACTATE UNIT AND ITS MANUFACTURING METHOD

This application is a 35 U.S.C. §371 National Stage entry of International Application No. PCT/KR2007/005852, filed on Nov. 21, 2007, and claims the benefit of Korean Application No. 10-2006-0115158, filed on Nov. 21, 2006, Korean Application No. 10-2006-0115159, filed on Nov. 21, 2006, Korean Application No. 10-2006-0115160, filed on Nov. 21, 2006, and Korean Application No. 10-2006-0115161, filed on Nov. 21, 2006, all of which are hereby incorporated by reference in its entirety.

TECHNICAL FIELD

The present invention relates to copolymer comprising 4-hydroxybutyrate monomer unit and lactate monomer unit or copolymer comprising 4-hydroxybutyrate monomer unit, lactate monomer unit and 3-hydroxyalkanoate monomer unit, and a method for manufacturing such polymer.

BACKGROUND ART

Polylactate (PLA) is a typical biodegradable polymer originated from lactate, which has a variety of applications as a common or a medical polymer. At present, PLA is being prepared by polymerizing lactate which is produced by fermenting microorganisms, but only low molecular weight PLA (1000-5000 dalton) is produced by direct polymerization of lactate. To synthesize high molecular weight (>100,000 dalton) of PLA, a method polymerizing low molecular weight PLA obtained by direct polymerization of lactate with a chain coupling agent can be used. However, the method has its disadvantages in that the process for preparing PLA of high molecular weight is complicated by the addition of a solvent or a chain coupling agent in which they are difficult to remove. At present, in the process for preparing commercially available PLA of high molecular weight, a method, in which lactate is converted into lactide to synthesize PLA by cyclodehydration of the lactide ring, is being used.

Meanwhile, polyhydroxyalkanoate (PHA) is a polyester which microorganisms accumulate therein as a carbon and energy storage compound when other nutritive elements, for example, phosphorus, nitrogen, magnesium, oxygen, are deficient while the carbon source is in excess. PHA is recognized as an alternative material for synthesized plastics since it has similar properties to synthetic polymers originating from petroleum, and, at the same time, shows an excellent biodegradation property.

The existing PHA is divided into SCL-PHA (short-chain-length PHA) having short carbon chains and MCL-PHA (medium-chain-length PHA) having long carbon chains. A gene synthesizing PHA was cloned from *Ralstonia eutropha*, *Pseudomonas* sp. microorganism, and PHA consisting of various monomers was synthesized by recombinant microorganisms (Qi et al., *FEMS Microbiol. Lett.*, 157:155, 1997; Qi et al., *FEMS Microbiol. Lett.*, 167:89, 1998; Langenbach et al., *FEMS Microbiol. Lett.*, 150:303, 1997; WO 01/55436; U.S. Pat. No. 6,143,952; WO 98/54329; and WO 99/61624).

To produce PHA in microorganisms, an enzyme which converts microorganisms' metabolites into a PHA monomer and PHA synthase which synthesizes a PHA polymer using the PHA monomers are required. PHA synthase synthesizes PHA using hydroxyacyl-CoA as a substrate and alpha-ketothiolase (PhaA), acetoacetyl-CoA reductase (PhaB), cloned from *Ralstonia eutropha* etc., 3-hydroxydecanoyl-ACP:CoA transferase (PhaG) cloned from *Pseudomonas* sp., (R)-specific enoyl-CoA hydratase (PhaJ) derived from *Aeromonas caviae* and *Pseudomonas aeruginosa* (Fukui et al., J. Bacteriol., 180:667, 1998; Tsage et al., FEMS Microbiol. Lett., 184:193, 2000), 3-ketoacyl-ACP reductase (FabG) derived from *E. coli, Pseudomonas aeruginosa*, etc. (Taguchi et al., FEMS Microbiol. Lett., 176:183, 1999; Ren et al., J. Bacteriol., 182:2978, 2000; Park et al., FEMS Microbiol. Lett., 214:217, 2002), phosphotransbutylase (Ptb) and butyrate kinase (Buk) derived from *Clostridium acetobutyricum* (Liu and Steinbuchel, Appl Environ Microbiol, 66:739, 2000), Cat2 derived from *Clostridium kluyveri* (Hein et al. FEMS Microbiol. Lett., 15:411, 1997), etc. are known as enzymes capable of generating hydroxyacyl-CoA which is a substrate of PHA. Various kinds of PHAs have been synthesized with these enzymes using hydroxyalkanoates hydroxylated at various positions in the carbon chain (mainly the 3, 4, 5, and 6 positions).

However, it has been reported that it has little PHA synthase activity on hydroxyalkanoate which is hydroxylated at the 2-position (Zhang et al., *Appl. Microbiol. Biotechnol.*, 56:131, 2001; Valentin and Steinbuchel, Appl. Microbiol. Biotechnol., 40:699, 1994). Thus far, there have been reports of PHA synthase activity on lactyl-CoA measured in vitro, but PHA synthase activity on lactyl-CoA is very weak (Zhang et al., *Appl. Microbiol. Biotechnol.*, 56:131, 2001; Valentin and Steinbuchel, *Appl. Microbiol. Biotechnol.*, 40:699, 1994). That is, there are no examples of natural production or production by recombinant cells of PHA and its copolymers because a hydroalkanoate, such as lactate hydroxylated at the 2-carbon position, is not a suitable substrate for PHA synthase.

U.S. Patent application publication no. 20040076982 discloses a method that lactate is made from glucose, and lactyl-CoA is biosynthesized from lactate, and 3-hydroxyalkanoate-CoA is biosynthesized from lactyl-CoA. However, the publication does not disclose a method for preparing copolymer with lactyl-CoA and 3-hydroxyalkanoate-CoA.

DISCLOSURE

Technical Problem

Accordingly, the object of the present invention is to provide a copolymer comprising 4-hydroxybutyrate monomer unit and lactate monomer unit or a copolymer comprising 4-hydroxybutyrate monomer unit, lactate monomer unit and 3-hydroxyalkanoate monomer unit.

Another object of the present invention is to provide a method for preparing the copolymer.

Technical Solution

To achieve the object, the present invention provides a copolymer comprising lactate monomer unit and 4-hydroxybutyrate monomer unit.

The present invention also provides a copolymer comprising lactate monomer unit, 4-hydroxybutyrate monomer and 3-hydroxyalkanoate monomer unit.

More preferably, the copolymer according to the present invention is 4-hydroxybutyrate-lactate copolymer (poly(4-hydroxybutyrate-co-lactate)), 4-hydroxybutyrate-3-hydroxypropionate-lactate terpolymer (poly(4-hydroxybutyrate-co-3-hydroxypropionate-co-lactate)), 3-hydroxybutylate-4-hydroxybutyrate-lactate terpolymer (poly(3-hydroxybutyrate-co-4-hydroxybutylate-co-lactate)), or 3-hydroxybutyrate-3-hydroxypropionate-4-hydroxybutyrate-lactate tetrapolymer (poly(3-hydroxybutyrate-co-3-hydroxypropionate-co-4-hydroxybutylate-co-lactate)).

The present invention also provides a method for preparing a copolymer comprising lactate monomer unit and 4-hydroxybutyrate monomer unit, wherein the method comprises culturing a cell or plant comprising (a) a gene of enzyme converting lactate into lactyl-CoA and converting 3-hydroxyalkanoate into 3-hydroxyalkanoyl-CoA, (b) phosphotransbutylase gene, (c) butyrate kinase gene and (d) polyhydroxyalkanoate (PHA) synthase gene together.

In the present invention, the cell or plant can be obtained by transforming a cell or plant not having at least one among the (a), (b), (c) and (d) genes with the gene(s) that the cell or plant does not have among the (a), (b), (c) and (d) genes. The cell or plant can be obtained also by transforming a cell or plant in which the expression of at least one among the (a), (b), (c) and (d) genes is weak or not present with the gene(s) whose expression is weak or not present.

That is, the cell or plant being able to synthesize the copolymer comprising 4-hydroxybutyrate monomer unit and lactate monomer unit can be obtained by (i) transforming a cell or plant not having any one of the genes with gene of enzyme converting lactate and 3-hydroxyalkanoate into lactyl-CoA and 3-hydroxyalkanoyl-CoA, respectively, phosphotransbutylase gene, butyrate kinase gene and PHA synthase gene, (ii) transforming a cell or plant having the gene of PHA synthase using lactyl-CoA as a substrate with gene of enzyme converting lactate and 3-hydroxyalkanoate into lactyl-CoA and 3-hydroxyalkanoyl-CoA, respectively, phosphotransbutylase gene and butyrate kinase gene, (iii) transforming a cell or plant having gene of enzyme converting lactate into lactyl-CoA with phosphotransbutylase gene, butyrate kinase gene and PHA synthase gene, (iv) transforming a cell or plant having phosphotransbutylase gene with gene of enzyme converting lactate and 3-hydroxyalkanoate into lactyl-CoA and 3-hydroxyalkanoyl-CoA, respectively, butyrate kinase gene and PHA synthase gene, (v) transforming a cell or plant having butyrate kinase gene with gene of enzyme converting lactate and 3-hydroxyalkanoate into lactyl-CoA and 3-hydroxyalkanoyl-CoA, respectively, phosphotransbutylase gene and PHA synthase gene, (vi) transforming a cell or plant having gene of PHA synthase using lactyl-CoA as a substrate and gene of enzyme converting lactate and 3-hydroxyalkanoate into lactyl-CoA and 3-hydroxyalkanoyl-CoA, respectively, with phosphotransbutylase gene and butyrate kinase gene, (vii) transforming a cell or plant having gene of enzyme converting lactate and 3-hydroxyalkanoate into lactyl-CoA and 3-hydroxyalkanoyl-CoA, respectively, and phosphotransbutylase gene with gene of PHA synthase using lactyl-CoA as a substrate and butyrate kinase gene, (viii) transforming a cell or plant having gene of enzyme converting 3-hydroxyalkanoate into 3-hydroxyalkanoyl-CoA and butyrate kinase gene with PHA synthase gene and phosphotransbutylase gene, (ix) transforming a cell or plant having gene of PHA synthase using lactyl-CoA as a substrate and butyrate kinase gene with gene of enzyme converting lactate and 3-hydroxyalkanoate into lactyl-CoA and 3-hydroxyalkanoyl-CoA, respectively, and phosphotransbutylase gene, (x) transforming a cell or plant having PHA synthase gene and phosphotransbutylase gene with gene of enzyme converting lactate and 3-hydroxyalkanoate into lactyl-CoA and 3-hydroxyalkanoyl-CoA, respectively, and butyrate kinase gene, (xi) transforming a cell or plant having phosphotransbutylase gene and butyrate kinase gene with gene of enzyme converting lactate and 3-hydroxyalkanoate into lactyl-CoA and 3-hydroxyalkanoyl-CoA, respectively, and gene of PHA synthase using lactyl-CoA as a substrate, (xii) transforming a cell or plant having gene of enzyme converting lactate and 3-hydroxyalkanoate into lactyl-CoA and 3-hydroxyalkanoyl-CoA, respectively, phosphotransbutylase gene and butyrate kinase gene with gene of PHA synthase using lactyl-CoA as a substrate, (xiii) transforming a cell or plant having phosphotransbutylase gene, butyrate kinase gene and PHA synthase gene with gene of enzyme converting lactate into lactyl-CoA, (xiv) transforming a cell or plant having gene of enzyme converting lactate and 3-hydroxyalkanoate into lactyl-CoA and 3-hydroxyalkanoyl-CoA, respectively, butyrate kinase gene and PHA synthase gene with phosphotransbutylase gene, or (xv) transforming a cell or plant having gene of enzyme converting lactate and 3-hydroxyalkanoate into lactyl-CoA and 3-hydroxyalkanoyl-CoA, respectively, phosphotransbutylase and PHA synthase gene with butyrate kinase gene. However, the scope of the present invention is not limited to the concrete examples described above.

Preferably, in the present invention, the gene of enzyme converting lactate and 3-hydroxyalkanoate into lactyl-CoA and 3-hydroxyalkanoyl-CoA, respectively, is propionyl-CoA transferase gene (pct).

Preferably, in the present invention, the phosphotransbutylase (Ptb) gene is derived from *Clostridium acetobutyricum*.

Preferably, in the present invention, the butyrate kinase (Buk) gene is derived from *Clostridium acetobutyricum*.

In the present invention, Cat2 gene derived from *Clostridium kluyveri* may be used instead of the Ptb gene and buk gene. The Cat2 gene is a enzyme converting 4-hydroxybutyrate into 4-hydroxybutyryl-CoA like the Ptb gene and buk gene. Preferably, the nucleotide sequence of Cat2 gene is SEQ ID No: 30.

Furthermore, in case that a gene encoding PHA synthase for which lactyl-CoA is a substrate is phaC, the cells or plants are transformed with a recombinant vector comprising pct, ptb and buk gene. At the same time, the cells or plants are transformed with a vector comprising phaC, or phaC is inserted into a chromosome. In addition, in case that a gene encoding PHA synthase for which lactyl-CoA is a substrate is phaC, the cells or plants are transformed with a recombinant vector comprising pct gene. At the same time, the cells or plants are transformed with a vector comprising phaC, or phaC is inserted into a chromosome.

As is known in the art, various microorganisms have a gene encoding PHA synthase (Korea Patent issued No. 10-250830). The following are examples of such microorganisms: microorganisms of the genus *Achromobacter* that include *Achromobacter* sp., *Achromobacter xylosoxidans*, etc., microorganisms of the genus *Acinetobacter* that include *Acidovorax delafieldii, Acidovax facilis, Acinetobacter* sp., *Acinetobacter calcoaceticus, Acinetobacter lwoffii*, etc., microorganisms of the genus *Aeromonas* that include *Actinomyces* sp., *Aeromonas caviae, Aeromonas hydrophila, Aeromonas salmonicida*, etc., microorganisms of the genus *Alcaligenes* that include *Alcaligenes aestus, Alcaligenes denitrificans, Alcaligenes eutrophus* (after renamed as *Ralstonia eutropha*, it is renamed as *Wautersia eutropha*), *Alcaligenes faecalis, Alcaligenes latus, Alcaligenes pacificus, Alcaligenes paradoxus, Alcaligenes venestus*, etc., microorganisms of the genus *Amoebobacter* that include *Alteromonas macleodii, Amoebobacter roseu, Amoebobacter pendens*, etc., microorganisms of the genus *Azospirillum* that include *Aphanocapa* sp., *Aphanothece* sp., *Aquaspirillum autotrophicum, Azorhizobium caulinodans, Azospirillum* sp., *Azospirillum brasilense, Azospirillum lipoferum*, etc., microorganisms of the genus *Azotobacter* that include *Azotobacter* sp., *Azotobacter agilis, Azotobacter chroococcum, Azotobacter macrocytogenes, Azotobacter vinelandii*, etc., microorganisms of the genus *Bacillus* that include *Bacillus anthracis, Bacillus cereus, Bacillus megaterium, Bacillus subtillus, Bacillus thuringiensis*, etc., microorganisms of the genus *Beggiatoa* that include *Beggiatoa* sp., *Beggiatoa alba*, etc., microorganisms of the genus *Beijerinckia* that include *Beijerinckia indicus, Beijerinckia mobilis*, etc., microorganisms of the genus *Beneckea* that include *Beneckea natrigens, Beneckea pelagia*, etc., microorganisms of the genus *Caulobacter* that include *Bordetella pertussis, Bradyrhizobium japonicum, Caryophamon latum, Caulobacter bacteroides, Caulobacter crescentus*, etc., microorganisms of the genus *Chlorogloea* that include *Chloroflexus aurantiacus, Chlorogloea fritschii*, etc., microorganisms of the genus *Chromatium* that include *Chromatium minutissimum, Chromatium okenii, Chromatium tepidum*, etc., microorganisms of the genus *Chromobacterium* that include *Chromobacterium violaceum*, etc., microorganisms of the genus *Clostridium* that include *Clostridium botulinum, Clostridium sphenoides*, etc., microorganisms of the genus *Comamonas* that include *Comamonas acidovorans, Comamonas testosteroni*, etc., microorganisms of the genus *Corynebacterium* that include *Corynebacterium autotrophicum, Corynebacterium hydrocarboxydans*, etc., microorganisms of the genus *Derxia* that include *Cyanobacteria, Derxia gummosa*, etc., microorganisms of the genus *Desulfonema* that include *Desulfococcus multivorans, Desulfonema limicola, Desulfonema magnum*, etc., microorganisms of the genus *Ectothiorhodospira* that include *Desulfosacina variabilis, Desulfovibrio sapovorans, Ectothiorhodospira halochloris, Ectothiorhodospira mobilis, Ectothiorhodospira vacuolata*, etc., microorganisms of the genus *Halobacterium* that include *Ferrobacillus ferroxidans, Flavobacterium* sp., *Haemophilus influenzae, Halobacterium gibbonsii, Halobacterium volcanii*, etc., microorganisms of the genus *Hydrogenophaga* that include *Haloferax mediterranei, Hydroclathratus clathratus, Hydrogenomonas facilis, Hydrogenophaga flava, Hydrogenophaga pseudoflava, Hydrogenophaga taeniospiralis*, etc., microorganisms of the genus *Hyphomicrobium* that include *Hyphomicrobium vulgare*, etc., microorganisms of the genus *Methylbacterium* that include *Ilyobater delafieldii, Labrys monachus, Lamprocystis reseopersicina, Lampropedia hyaline, Legionella* sp., *Leptothrix discophorus, Methylbacterium* AM1, *Methylbacterium extorquens*, etc., microorganisms of the genus *Methylosinus* that include *Methylococcus thermophilus, Methlocystis parvus, Methylomonas methanica, Methylosinus sporium, Methylosinus trichosporium*, etc., microorganisms of the genus *Micrococcus* that include *Methylovibrio soehngenii, Micrococcus denitrificans, Micrococcus halodenitrificans*, etc., microorganisms of the genus *Mycobacterium* that include *Mycobacterium album, Mycobacterium vacae*, etc., microorganisms of the genus *Nitrobacter* that include *Nitrobacter agilis, Nitrobacter winogradskyi*, etc., microorganisms of the genus *Nocardia* that include *Nocardia alba, Nocardia asteroides, Nocardia lucida, Nocardia rubra*, etc., microorganisms of the genus *Photobacterium* that include *Paracoccus dentrificans, Oscillatoria limosa, Penicillium cyclopium, Photobacterium mandapamensis, Photobacterium phosphoreum*, etc., microorganisms of the genus *Pseudomonas* that include *Physarum ploycephalum* and *Pseudomonas glathei, Pseudomonas indigofera, Pseudomonas lemonieri, Pseudomonas mallei, Pseudomonas marina, Pseudomonas mixta, Pseudomonas oleovorans, Pseudomonas oxalaticus, Pseudomonas pseudoalcaligenes, Pseudomonas aeruginosa, Pseudomonas alcaligenes, Pseudomonas asplenii, Pseudomonas butanovora, Pseudomonas cepacia, Pseudomonas coronafaciens, Pseudomonas dacunhae, Pseudomonas denitrificans, Pseudomonas diminuta, Pseudomonas echinoides, Pseudomonas fluorescens, Pseudomonas putida, Pseudomonas rubrilineas, Pseudomonas saccharophila, Pseudomonas stutzeri, Pseudomonas syringae, Pseudomonas thermophilus, Pseudomonas viridiflava*, etc., microorganisms of the genus *Ralstonia*, microorganisms of the genus *Rhizobium* that include *Rhizobium hedysarum, Rhizobium lupini, Rhizobium meliloti, Rhizobium phaseoli, Rhizobium trifoli*, etc., microorganisms of the genus *Rhodobacillus*, microorganisms of the genus *Rhodobacter* that include *Rhodobacter capsulatus, Rhodobacter sphaeroides*, etc., microorganisms of the genus *Rhodococcus* that include *Rhodococcus rhodochrous*, etc., microorganisms of the genus *Rhodocyclus* that include *Rhodocyclus gelatinosus, Rhodocyclus tenuis*, etc., microorganisms of the genus *Rhodopseudomonas* that include *Rhodomicrobium vannielii* and *Rhodopseudomonas acidophila, Rhodopseudomonas capsulata*, etc., microorganisms of the genus *Rhodospirillum* that include *Rhodospirillum molischianum, Rhodospirillum rubrum*, etc., microorganisms of the genus *Spirillum* that include *Sphingomonas paucimobilis, Spirillum itersomii, Spirillum serpens*, etc., microorganisms of the genus *Spirulina* that include *Spirulina jenneri, Spirulina maxima, Spirulina subsaksa*, etc., microorganisms of the genus *Staphylococcus* that include *Staphylococcus aureus, Staphylococcus epidermidis, Staphylococcus xylosus*, etc., microorganisms of the genus *Stella* that include *Stella humosa, Stella vacuolata*, etc., microorganisms of the genus *Streptomyces* that include *Streptomyces antibioticus, Streptomyces coelicolor*, etc., microorganisms of the genus *Thiobacillus* that include *Syntrophomonas wolfei, Thermophilic cyanobacteria, Thermus thermophilus, Thiobacillus* A2, *Thiobacillus acidophilus, Thiobacillus versutus*, etc., microorganisms of the genus *Thiocapsa* that include *Thiocapsa pfennigii*, etc., microorganisms of the genus *Zoogloea* that include *Thiocystis violacea, Vibrio parahaemolyticus, Xanthobacter autotrophicus, Xanthomonas maltophilia, Zoogloea ramigera*, etc.

Preferably, the polyhydroxyalkanoate (PHA) synthase gene of the present invention is phaC1$_{ps6-19}$ originated from *Pseudomonas* sp. 6-19. More preferably, the PHA synthase gene encodes the amino acid sequence of SEQ ID NO: 8 having mutations of: a) S325T and Q481M; b) E130D and Q481K; c) S325T and Q481K; d) E130D and Q481M; e) E130D and Q481R; f) E130D, S325T and Q481M; g) E130D, S325T and Q481K; h) E130D, S477R and Q481K; i) E130D, S477R and Q481M; j) E130D, S477R and Q481R; k) E130D, S477H and Q481K; l) E130D, S477H and Q481M; m) E130D, S477H and Q481R; n) E130D, S477F and Q481K; o) E130D, S477F and Q481M; p) E130D, S477F and Q481R; q) E130D, S477Y and Q481K; r) E130D, S477Y and Q481M; s) E130D, S477Y and Q481R; t) E130D, S325T, S477R and Q481M; u) E130D, S325T, S477R and Q481K; v) E130D, S325T, S477F and Q481M; w) E130D, S325T, S477G and Q481M; or x) E130D, S325T, S477F and Q481K. These PHA synthase mutants are more preferable in aspect of using lactyl-CoA as a substrate.

In the present invention, the cell is preferably a microorganism. More preferably, the microorganism is *E. Coli*.

In the present invention, the cell or plant having the gene of enzyme converting lactate and 3-hydroxyalkanoate into lactyl-CoA and 3-hydroxyalkanoyl-CoA, respectively, phosphotransbutylase gene, butyrate kinase gene and polyhydroxyalkanoate (PHA) synthase gene together can be cultured in a medium comprising at least one selected from the group consisting of 4-hydroxybutyrate, 3-hydroxypropionate and 3-hydroxybutyrate to produce a copolymer comprising 4-hydroxybutyrate monomer unit, lactate monomer unit and optionally 3-hydroxyalkanoate. If the cell or plant can biosynthesize lactate, 4-hydroxybutyrate and 3-hydroxyalkanoate from other carbon sources such as glucose, citric acid, etc., there may be no need to further add 4-hydroxybutyrate, lactate and so on to the medium.

For example, poly(4-hydroxybutyrate-co-3-hydroxypropionate-co-lactate) can be prepared by culturing the cell or plant in a medium further comprising 4-hydroxybutyrate (4-HB) and 3-hydroxypropionate (3-HP).

For example, 3-hydroxybutyrate-3-hydroxypropionate-4-hydroxybutyrate-lactate tetrapolymer can be prepared by culturing the cell or plant in a medium further comprising 4-hydroxybutyrate (3-HP), 3-hydroxypropionate (3-HP) and 3-hydroxybutyrate (3-HB).

Transformation of plants for preparing plant comprising genes of transferase and synthase can be achieved by conventional methods using *Agrobacterium* or virus vectors. For example, transformed plants are obtained by transforming an *Agrobacterium* with a recombinant vector containing the inventive gene and infecting a tissue, etc. of the target plant with the transformed *Agrobacterium*. More specifically, the transformed plant can be prepared by pre-culturing an explant of plant of interest, and then transforming the explant by co-cultivating the explant and a transformed *Agrobacterium*; culturing said infected explants to induce callus; and excising obtained callus, and culturing it in shoot-inducing medium.

The term "explant," as used herein, means a tissue fragment cut from a plant, and includes cotyledon or hypocotyl. Cotyledon or hypocotyls can be used as the explant of the present invention. It is more preferable to use cotyledon obtained by disinfecting and washing seeds of the plant, and germinating it in MS medium.

Transformed plants useful for the present invention include, but are not limited to, tobacco, tomato, red peppers, beans, rice, and corn. Also, even though a transformed plant is one that propagates sexually, it will be obvious to a person skilled in the art that such a plant can be reproduced asexually using plant tissue culture, etc.

MODES FOR CARRYING OUT THE INVENTION

Hereinafter, the present invention is described in considerable detail. The following examples are offered by way of illustration to help those skilled in the art understand the present invention, and are not intended to limit the scope of the invention.

Example 1

Construction of a Recombinant Plasmid Comprising PCT Gene and PHA Synthase Gene

Recombinant plasmids, pPs619C1300-CPPCT and pTac-CpPctNCvEC, comprising pct gene and PHA synthase gene are constructed to prepare a copolymer comprising 4-hydroxybutyrate unit and lactate unit.

(1) Construction of Plasmid pPs619C1300-CPPCT

Propionyl-CoA transferase (CP-PCT) gene derived from *Clostridium propionicum* was used as the pct gene, and PHA synthase gene derived from *Pseudomonas* sp. 6-19 was used as the PHA synthase gene.

Figure 1:
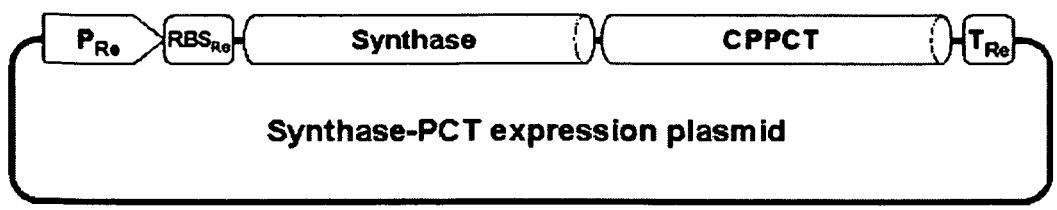
FIG. 1 is a simple diagram of constitutive expression vector expressing PHA synthase and CP-PCT together.

The operon of constitutive expression system expressing PHA synthase and CP-PCT together was constructed like FIG. 1. CP-PCT was well known to have toxicity to host microorganism. That is, in tac promoter or T7 promoter expression system induced by IPTG (this system is widely used in expression of a recombinant protein), all microorganisms become dead shortly after the addition of inducer. Because of this reason, it is thought as suitable to use expression system in which it is weakly expressed, but continuously expressed according to the growth of microorganism. CP-PCT gene was obtained by PCR using the chromosome DNA of *Clostridium propionicum* (DSM1682) as template and the primers of SEQ ID NO: 1 and SEQ ID NO: 2 made based on pct gene sequence (Selmer et al., *Eur J Biochem.*, 269:372, 2002). The nucleotide sequence is shown in SEQ ID NO: 29.

```
SEQ ID NO: 1:
5-ggaattcATGAGAAAGGTTCCCATTATTACCGCAGATGA

SEQ ID NO: 2:
5-gctctagattaggacttcatttccttcagacccattaagccttctg
```

NdeI restriction enzyme site of wild CP-PCT was removed by SDM method for easiness of cloning. In addition, overlapping PCR was performed with the primers of SEQ ID NO: 3 and 4 to add SbfI/NdeI recognition site.

```
SEQ ID NO: 3:
5-agg cct gca ggc gga taa caa ttt cac aca gg-3

SEQ ID NO: 4:
5-gcc cat atg tct aga tta gga ctt cat ttc c-3
```

To separate the gene of PHA synthase (phaC1$_{Ps6-19}$) originated from *Pseudomonas* sp. 6-19 (KCTC 11027BP), total DNA of *Pseudomonas* sp. 6-19 was extracted, and the primers of SEQ ID NO: 5 and 6 were prepared based on the sequence of phaC1$_{Ps6-19}$ gene (Ae-jin Song, Master's Thesis, Department of Chemical and Biomolecular Engineering, KAIST, 2004) and PCR was performed to get the gene of phaC1$_{Ps6-19}$. The nucleotide sequence of phaC1$_{Ps6-19}$ gene is shown in SEQ ID NO: 7, from which the amino acid sequence evaluated is shown in SEQ ID NO: 8.

SEQ ID NO: 5:
5-GAG AGA CAA TCA AAT CAT GAG TAA CAA GAG TAA CG-3

SEQ ID NO: 6:
5-CAC TCA TGC AAG CGT CAC CGT TCG TGC ACG TAC-3

The above obtained phaC1$_{Ps6-19}$ gene was inserted into BstBI/SbfI site of pBluescript II (Stratagene Co., USA) to make pPs619C1 recombinant vector. BstBI sites contained inside were removed by SDM (site directed mutagenesis) method without mutation of amino acid to make phaC1$_{Ps6-19}$ synthase gene fragment having two BstBI/SbfI sites only at the both ends, and overlapping PCR were performed with the primers of SEQ ID NO: 9 and 10, SEQ ID NO: 11 and 12, and SEQ ID NO: 13 and 14 to add BstBI/SbfI-recognition site.

SEQ ID NO: 9:
5-atg ccc gga gcc ggt tcg aa-3

SEQ ID NO: 10:
5-CGT TAC TCT TGT TAC TCA TGA TTT GAT TGT CTC TC-3

SEQ ID NO: 11:
5-GAG AGA CAA TCA AAT CAT GAG TAA CAA GAG TAA CG-3

SEQ ID NO: 12:
5-CAC TCA TGC AAG CGT CAC CGT TCG TGC ACG TAC-3

SEQ ID NO: 13:
5-GTA CGT GCA CGA ACG GTG ACG CTT GCA TGA GTG-3

SEQ ID NO: 14:
5-aac ggg agg gaa cct gca gg-3

Three positions (130, 325, and 481) of amino acid affecting SCL (short-chain-length PHA) synthesis activity of phaC1$_{Ps6-19}$ synthase were found out through amino acid sequence alignment analysis, and pPs619C1300 comprising the gene encoding the mutant having mutations of E130D, S325T and Q481M in the amino acid sequence phaC1$_{Ps6-19}$ synthase was constructed by SDM method. The phaC1$_{Ps6-19}$ synthase mutant was shown in table 1 below.

TABLE 1

| Recombinant vector | Necleic acid substitution | Amino acid substitution | Primer |
|---|---|---|---|
| pPs619C1300 | GAA → GAT | E130D | SEQ ID NO: 15/16 |
|  | AGC → ACC | S325T | SEQ ID NO: 17/18 |
|  | CAG → ATG | Q481M | SEQ ID NO: 19/20 |

SEQ ID NO: 15: 5-atc aac ctc atg acc gat gcg atg gcg ccg acc-3
SEQ ID NO: 16: 5-ggt cgg cgc cat cgc atc ggt cat gag gtt gat-3
SEQ ID NO: 17: 5-CTG ACC TTG CTG GTG ACC GTG CTT GAT ACC ACC-3
SEQ ID NO: 18: 5-GGT GGT ATC AAG CAC GGT CAC CAG CAA GGT CAG-3
SEQ ID NO: 19: 5-CGA GCA GCG GGC ATA TC A TGA GCA TCC TGA ACC CGC-3
SEQ ID NO: 20: 5-GCG GGT TCA GGA TGC TCA TGA TAT GCC GCT GCT CG-3

Figure 2:
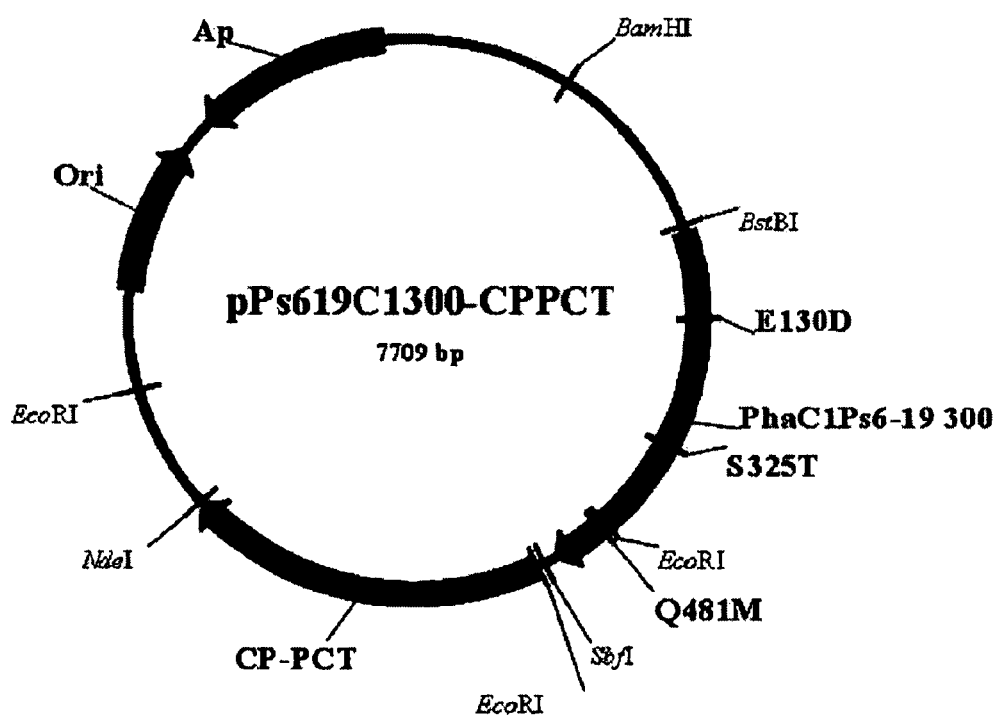
FIG. 2 is a gene map of recombinant plasmid pPs619C1300-CPPCT comprising PHA synthase gene and CP-PCT gene according to the present invention.

The obtained pPs619C1300 vector was excised with SbfI/NdeI, and the cloned CP-PCT gene was inserted into SbfI/NdeI recognition site to construct the pPs619C1300-CPPCT recombinant vector (FIG. 2).

(2) Construction of pTacCpPctNCvEC Plasmid pTac99A vector (Park and Lee, J. Bacteriol. 185, 5391-5397, 2003) was cut with SspI to get a gene fragment comprising Tac promoter and transcription terminator, and the fragment was inserted into pTrc99A (Pharmacia Biotech, Sweden) exercised with restriction enzyme SspI to make pTaclac vector. phaEC gene was amplified with the chromosome DNA of Chromatium vinosum (DSMZ180) as template and the primers of SEQ ID NO: 21 and 22.

SEQ ID NO: 21:
ggaaatc cat ATGACGATGTTCTCGCTCATGGCG

SEQ ID NO: 22:
ggaaatc catatg atc cag ggc cac tat ctc caa ctg

Figure 3:
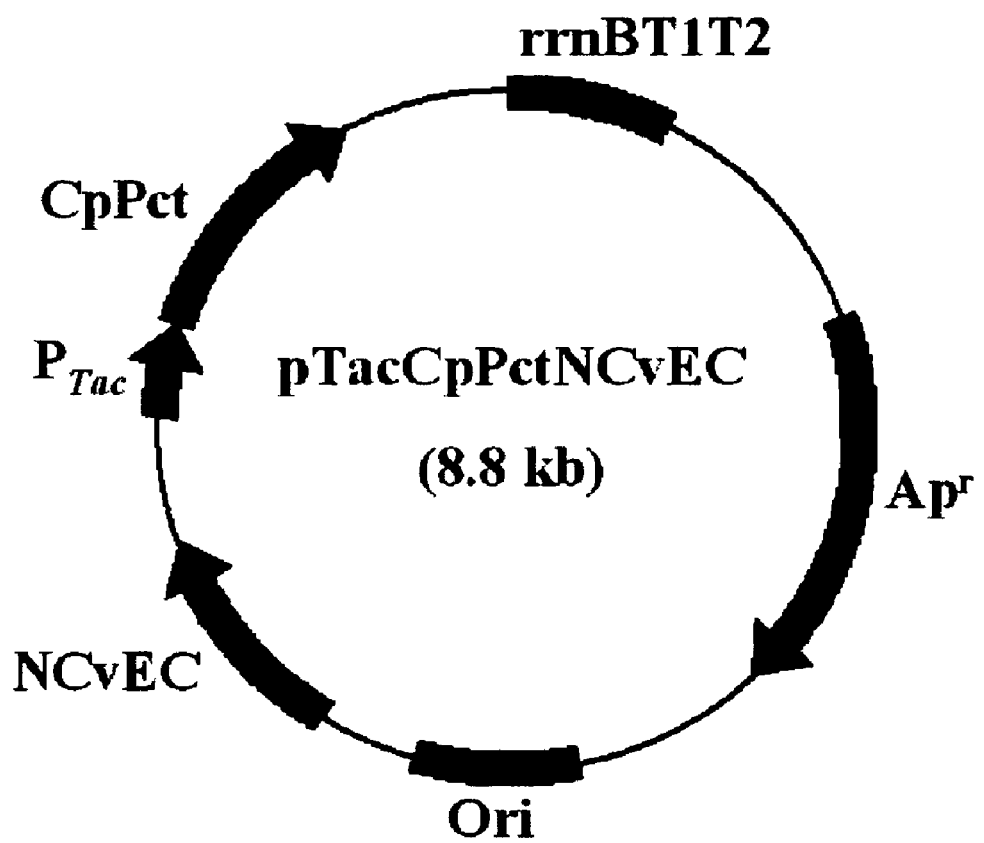
FIG. 3 is a gene map of recombinant plasmid pTacCpPct-NCvEC comprising PHA synthase gene and CP-PCT gene according to the present invention.

The amplified phaEC gene was inserted into the NdeI-excised site of the pTaclac vector to make pTaclacNCvEC vector. In addition, pct gene was obtained by cutting pPs619C1300-CPPCT with EcoRI/XbaI, and the pct gene was inserted into the EcoRI/XbaI-excised pTaclacNCvEC to make pTacCpPctNCvEC (FIG. 3).

(3) Construction of pMCSPtbBuk Plasmid ptb and buk gene was constructed as one operon in Clostridium acetobutyricum strain, and those nucleotide sequence were shown in SEQ ID NO: 27 and 28, respectively. ptb/buk gene was amplified with the primers of SEQ ID NO: 23 and 24 from the chromosome DNA of Clostridium acetobutyricum (ATCC824).

SEQ ID NO: 23:
GGCAGAGAG ACAATCAAAT C ATGATTAAGAGTTTTAATG

SEQ ID NO: 24:
ggaattc catatg tta ttt gta ttc ctt agc ttt ttc ttc tcc

Further, PCR using pC1300-CPPCT as template was performed with the primers of SEQ ID NO: 25 and 26 to amplify the gene of SbfI recognition site in pC1300-CPPCT.

SEQ ID NO: 25:    GGGCAGATGT GCCGGCAGAC

SEQ ID NO: 26:    gat ttg att gtc tct ctg ccg

Figure 4:
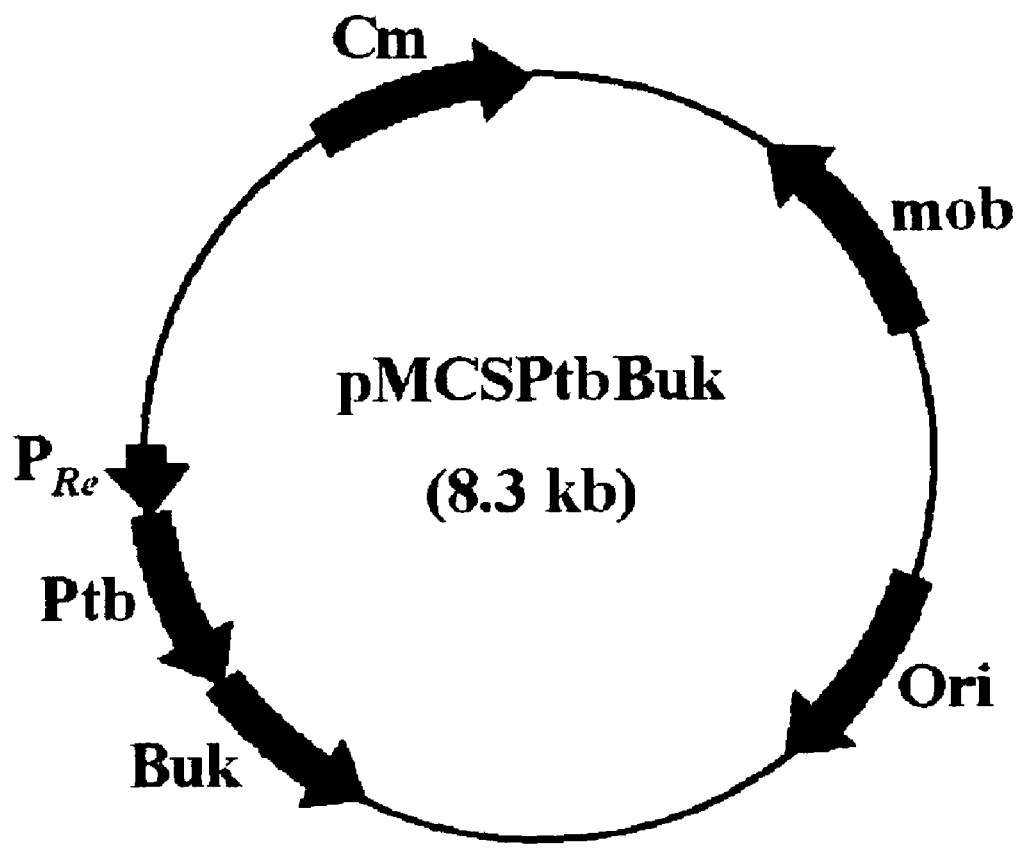
FIG. 4 is a gene map of recombinant plasmid pMCSPtbBuk comprising Ptb and Buk gene according to the present invention.

Overlapping PCR using the gene fragment obtained with the primers of SEQ ID NO: 23 and 24 and the gene fragment obtained with the primers of SEQ ID NO: 25 and 25 as templates was performed with the primers of SEQ ID NO: 24 and 25 to finally get ptb/buk gene fragment comprising SbfI/NdeI recognition site. The obtained ptb/buk gene fragment was cut with SbfI/NdeI, and then was inserted into pC1300-CPPCT excised with the same enzyme to get pPtbBuk plasmid. pPtbBuk plasmid was cut with XmaI/XhoI to get the gene fragment comprising the promoter of R. eutropha PHA biosynthesis gene and ptb/buk gene, and the obtained gene was inserted into pBBR1MCS (NCCB 3433) cut with XmaI/XhoI to get pMCSPtbBuk plasmid (FIG. 4).

Example 2

Preparation of 4-hydroxybutyrate-lactate copolymer

E. coli Top 10 (Invitrogen) was transformed with the pPs619C1300-CPPCT obtained in example 1 and pMCSPtbBuk together to get E. coli Top10/pPs619C1300-CPPCT/pMCSPtbBuk.

The transformant was cultured by two steps to get 4-hydroxybutyrate-lactate copolymer as follows: First, the transformed recombinant E. coli Top10/pPs619C1300-CPPCT/pMCSPtbBuk was cultured for 24 hours in 100 mL of LB medium (Bacto™ Triptone(BD) 10 g/L, Bacto™ yeast extract(BD) 5 g/L; NaCl (amresco) 10 g/L) containing 100 mg/L of ampicillin and 30 mg/L of chloramphenicol, and then the medium was centrifuged for 15 minutes at 4° C., 1000 g to collect cells.

Collected cells was anaerobically cultured for 3 days in MR medium (Glucose 10 g, KH$_2$PO$_4$ 6.67 g, (NH$_4$)$_2$HPO$_4$ 4 g, MgSO$_4$.7H$_2$O 0.8 g, citric acid 0.8 g and trace metal solution 5 mL per 1 L; Trace metal solution composition: 5M HCl 5 mL, FeSO$_4$.7H$_2$O 10 g, CaCl$_2$ 2 g, ZnSO$_4$.7H$_2$O 2.2 g, MnSO$_4$.4H$_2$O 0.5 g, CuSO$_4$.5H$_2$O 1 g, (NH$_4$)$_6$Mo$_7$O$_2$.4H$_2$O 0.1 g, and Na$_2$B$_4$O$_2$.10H$_2$O 0.02 g per 1 L) further comprising 2 g/L of 4-hydroxybutyrate (4-HB) and 100 mg/L of ampicillin and 30 mg/L of chloramphenicol.

The culture medium was centrifuged for 15 minutes at 4° C., 1000 to collect cells, and the cells was washed 4 times with lots of distilled water and dried for 12 hours at 80° C. Completely dried cells was quantified, and reacted with methanol at 100° C. in chloroform solvent under the catalyst of sulfuric acid. Half volume of distilled water was added at room temperature to the chloroform, and mixed. Then, the mixture was settled until separated into two layers. In two layers, the chloroform layer dissolving methylated monomer was collected, and the ingredients of the polymer were analyzed with gas chromatography. Benzoate was used as internal standard.

Figure 5:
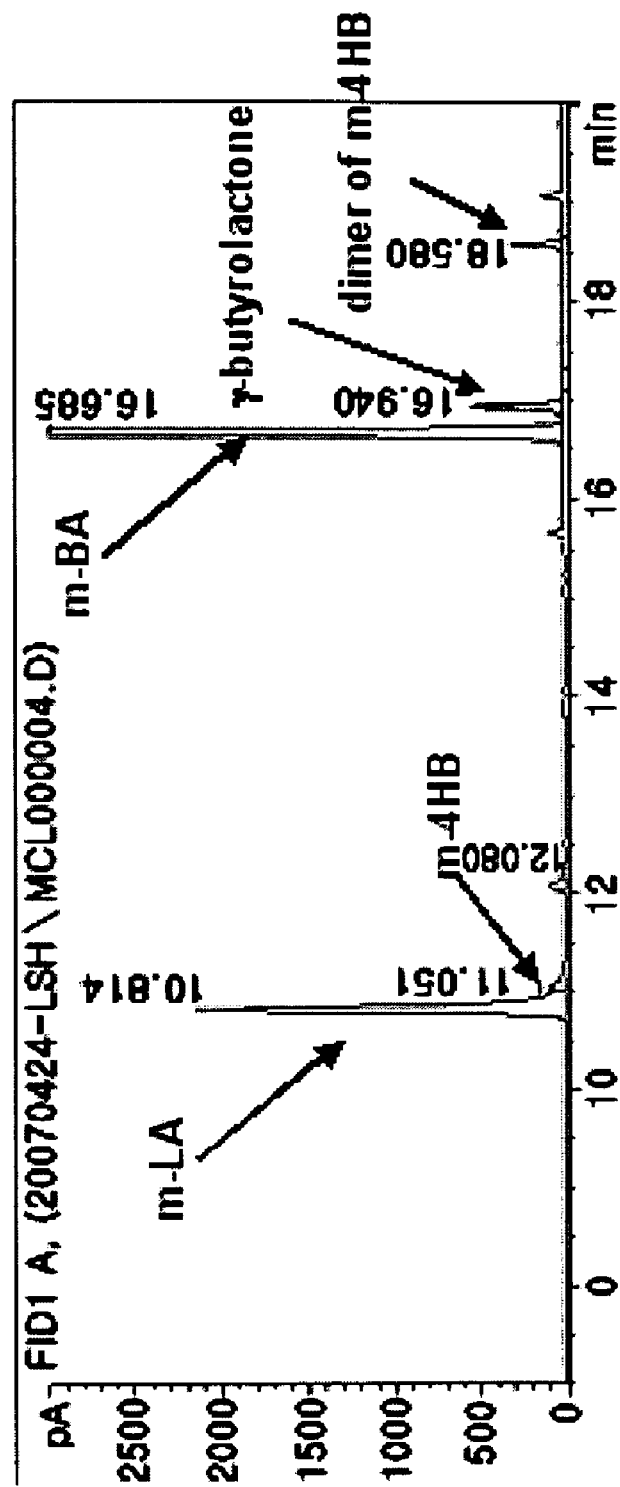
FIG. 5 is a NMR result of 4-hydroxybutyrate-lactate copolymer prepared by the recombinant *E. coli* transformed with pPs619C1300-CPPCT/pMCSPtbBuk plasmid.

As a result of the analysis, methyl-4-hydroxybutyrate and methyl-lactate were detected in $E.$ $coli$ Top10/pPs619C1300-CPPCT/pMCSPtbBuk transformant, which meant that new 4 hydroxybutyrate-lactate copolymer (poly(4-hydroxybutyrate-co-lactate)) was prepared by the recombinant $E.$ $coli$. NMR result of the obtained poly(4-hydroxybutyrate-co-lactate) copolymer was shown in FIG. 5.

Example 3

Preparation of 4-hydroxybutyrate-3-hydroxypropionate-lactate terpolymer

Figure 6:
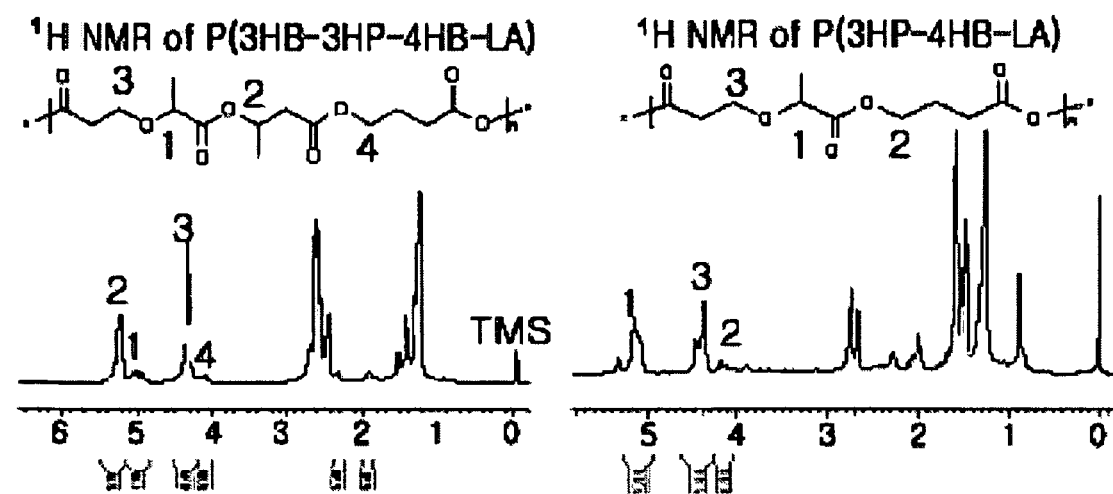
FIG. 6 is NMR results of 3-hydroxypropionate-4-hydroxybutyrate-lactate terpolymer and 3-hydroxybutyrate-3-hydroxypropionate-4-hydroxybutyrate-lactate tetrapolymer prepared by the recombinant *E. coli* transformed with pPs619C1300-CPPCT/pMCSPtbBuk plasmid.
Figure 7:
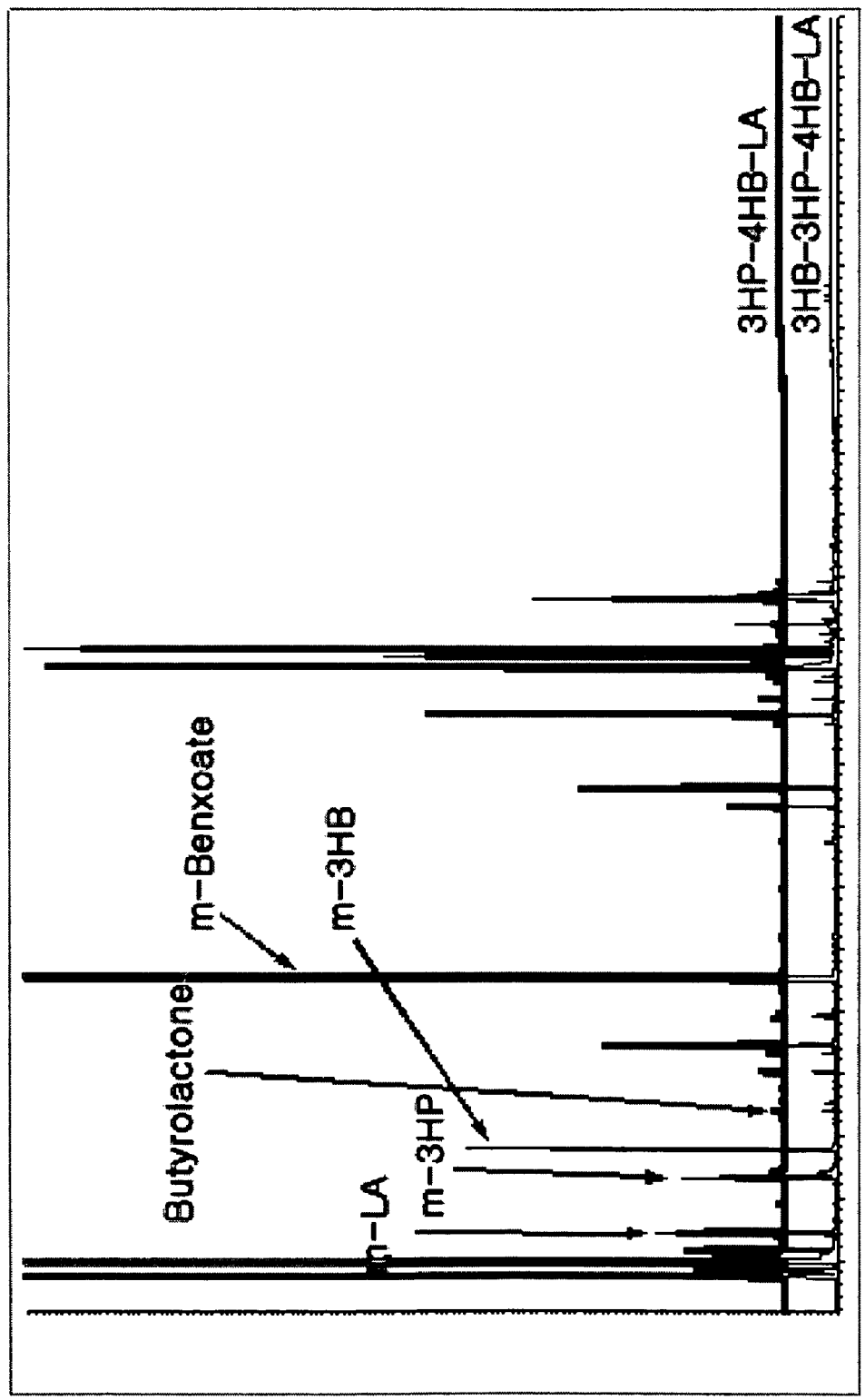
FIG. 7 is GC-MSD results of 3-hydroxypropionate-4-hydroxybutyrate-lactate terpolymer and 3-hydroxybutyrate-3-hydroxypropionate-4-hydroxybutyrate-lactate tetrapolymer prepared by the recombinant *E. coli* transformed with pPs619C1300-CPPCT/pMCSPtbBuk plasmid.

4-Hydroxybutyrate-3-hydroxypropionate-lactate terpolymer was prepared according to the method of example 2 except that the collected cells was anaerobically cultured for 3 days in MR medium further containing 2 g/L of 4-hydroxybutyrate (4-HB), 2 g/L of 3-hydroxypropionate (3-HP), 100 mg/L of ampicillin and 30 mg/L of chloramphenicol instead of MR medium further containing g/L of 4-HB, 100 mg/L of ampicillin and 30 mg/L of chloramphenicol. —As a result of the analysis, methyl-4-hydroxybutyrate, methyl-3-hydroxypropionate and methyl-lactate were detected in $E.$ $coli$ Top10/pPs619C1300-CPPCT/pMCSPtbBuk transformant, which meant that new 4-hydroxybutyrate-3-hydroxypropionate-lactate terpolymer [poly(4-hydroxybutyrate-co-3-hydroxypropionate-co-lactate)] was prepared by the recombinant $E.$ $Coli.$ $^1$H-NMR and GC-MSD results of the obtained 4-hydroxybutyrate-3-hydroxypropionate-lactate terpolymer were shown in FIGS. 6 and 7, respectively.

Example 4

Preparation of 3-hydroxybutyrate-4-hydroxybutyrate-lactate copolymer

3-Hydroxybutyrate-4-hydroxybutyrate-lactate terpolymer was prepared according to the method of example 2 except that the collected cells was anaerobically cultured for 3 days in MR medium further containing 2 g/L of 4-hydroxybutyrate (4-HB), 1 g/L of 3-hydroxybutyrate (3-HB), 100 mg/L of ampicillin and 30 mg/L of chloramphenicol instead of MR medium further containing g/L of 4-HB, 100 mg/L of ampicillin and 30 mg/L of chloramphenicol.

As a result of the analysis, methyl-4-hydroxybutyrate, methyl-3-hydroxybutyrate and methyl-lactate were detected in $E.$ $coli$ Top10/pPs619C1300-CPPCT/pMCSPtbBuk transformant, which meant that 3-hydroxybutyrate-4-hydroxyburyrate-lactate terpolymer [poly(3-hydroxybutyrate-co-4-hydroxybutyrate-co-lactate)] was prepared by the recombinant $E.$ $coli.$ Example 5

Preparation of 3-hydroxybutyrate-3-hydroxypropionate-4-hydroxybutyrate-lactate tetrapolymer 3 hydroxybutyrate-3-hydroxypropionate-4-hydroxybutyrate-lactate tetrapolymer was prepared according to the method of example 2 except that the collected cells was anaerobically cultured for 3 days in MR medium further containing 2 g/L of 3-hydroxybutyrate (3-HB), 2 g/L of 3 hydroxypropionate (3-HP), 1 g/L of 4-hydroxybutyrate (4-HB) and 100 mg/L of ampicillin instead of MR medium further containing 2 g/L of 4-HB, 100 mg/L of ampicillin and 30 mg/L of chloramphenicol.

As a result of the analysis, methyl-4-hydroxybutyrate, methyl-3-hydroxybutyrate, methyl-3-hydroxypropionate and methyl-lactate were detected in $E.$ $coli$ Top10/pPs619C1300-CPPCT/pMCSPtbBuk transformant, which meant that 3-hydroxybutyrate-3-hydroxypropionate-4-hydroxybutyrate-lactate tetrapolymer was prepared by the recombinant $E.$ $coli.$ $^1$H-NMR and GC-MSD results of the obtained 3-hydroxybutyrate-3-hydroxypropionate-4-hydroxybutyrate-lactate tetrapolymer were shown in FIGS. 6 and 7, respectively.

Example 6

Preparation of Various Mutants

Various PHA synthase mutants were prepared like the construction of the pPs619C1300 with the primers below. Obtained mutants were shown in tables 2, 3, 4 and 5.

```
E130D
SEQ ID NO: 15:
5'-atc aac ctc atg acc gat gcg atg gcg ccg acc-3'

SEQ ID NO: 16:
5'-ggt cgg cgc cat cgc atc ggt cat gag gtt gat-3'

S325T
SEQ ID NO: 17:
5'-CTG ACC TTG CTG GTG ACC GTG CTT GAT ACC ACC-3'

SEQ ID NO: 18:
5'-GGT GGT ATC AAG CAC GGT CAC CAG CAA GGT CAG-3'

S477R
SEQ ID NO: 31:
5'-gaa ttc gtg ctg tcg agc cgc ggg cat atc-3'

SEQ ID NO: 32:
5'-gat atg ccc gcg gct cga cag cac gaa ttc-3'

S477H
SEQ ID NO: 33:
5'-gaa ttc gtg ctg tcg agc cat ggg cat atc-3'

SEQ ID NO: 34:
5'-gat atg ccc atg gct cga cag cac gaa ttc-3'

S477F
SEQ ID NO: 35:
5'-gaa ttc gtg ctg tcg agc ttt ggg cat atc-3'

SEQ ID NO: 36:
5'-gat atg ccc aaa gct cga cag cac gaa ttc-3'
S477Y
```

-continued

SEQ ID NO: 37:
5'-gaa ttc gtg ctg tcg agc tat ggg cat atc-3'

SEQ ID NO: 38:
5'-gat atg ccc ata gct cga cag cac gaa ttc-3'

S477G
SEQ ID NO: 39:
5'-gaa ttc gtg ctg tcg agc ggc ggg cat atc-3'

SEQ ID NO: 40:
5'-gat atg ccc gcc gct cga cag cac gaa ttc-3'

Q481K
SEQ ID NO: 41:
5'-ggg cat atc aaa agc atc ctg aac ccg c-3'

SEQ ID NO: 42:
5'-gcg ggt tca gga tgc ttt tga tat gcc c-3'

Q481M
SEQ ID NO: 43:
5'-ggg cat atc atg agc atc ctg aac ccg c-3'

SEQ ID NO: 44:
5'-gcg ggt tca gga tgc tca tga tat gcc c-3'

Q481R
SEQ ID NO: 45:
5'-ggg cat atc cgc agc atc ctg aac ccg c-3'

SEQ ID NO: 46:
5'-gcg ggt tca gga tgc tgc gga tat gcc c-3'

TABLE 2

| Recombinant synthase | Nucleic acid substitution | Amino acid substitution | Primers |
|---|---|---|---|
| pPs619C1200 | AGC → ACC | S325T | SEQ ID NO: 17, 18 |
|  | CAG → ATG | Q481M | SEQ ID NO: 43, 44 |
| pPs619C1202 | GAA → GAT | E130D | SEQ ID NO: 15, 16 |
|  | CAG → AAA | Q481K | SEQ ID NO: 41, 42 |
| pPs619C1203 | AGC → ACC | S325T | SEQ ID NO: 17, 18 |
|  | CAG → AAA | Q481K | SEQ ID NO: 41, 42 |
| pPs619C1204 | GAA → GAT | E130D | SEQ ID NO: 15, 16 |
|  | CAG → ATG | Q481M | SEQ ID NO: 43, 44 |
| pPs619C1205 | GAA → GAT | E130D | SEQ ID NO: 15, 16 |
|  | GAG → CGC | Q481R | SEQ ID NO: 45, 46 |

TABLE 3

| Recombinant synthase | Nucleic acid substitution | Amino acid substitution | Primers |
|---|---|---|---|
| pPs619C1300 | GAA → GAT | E130D | SEQ ID NO: 15, 16 |
|  | AGC → ACC | S325T | SEQ ID NO: 17, 18 |
|  | CAG → ATG | Q481M | SEQ ID NO: 43, 44 |
| pPs619C1301 | GAA → GAT | E130D | SEQ ID NO: 15, 16 |
|  | AGC → ACC | S325T | SEQ ID NO: 17, 18 |
|  | CAG → AAA | Q481K | SEQ ID NO: 41, 42 |
| pPs619C1304 | GAA → GAT | E130D | SEQ ID NO: 15, 16 |
|  | AGC → CGC | S477R | SEQ ID NO: 31, 32 |
|  | CAG → AAA | Q481K | SEQ ID NO: 41, 42 |
| pPs619C1305 | GAA → GAT | E130D | SEQ ID NO: 15, 16 |
|  | AGC → CGC | S477R | SEQ ID NO: 31, 32 |
|  | CAG → ATG | Q481M | SEQ ID NO: 43, 44 |
| pPs619C1306 | GAA → GAT | E130D | SEQ ID NO: 15, 16 |
|  | AGC → CGC | S477R | SEQ ID NO: 31, 32 |
|  | CAG → CGC | Q481R | SEQ ID NO: 45, 46 |
| pPs619C1307 | GAA → GAT | E130D | SEQ ID NO: 15, 16 |
|  | AGC → CAT | S477H | SEQ ID NO: 33, 34 |
|  | CAG → AAA | Q481K | SEQ ID NO: 41, 42 |
| pPs619C1308 | GAA → GAT | E130D | SEQ ID NO: 15, 16 |
|  | AGC → CAT | S477H | SEQ ID NO: 33, 34 |
|  | CAG → ATG | Q481M | SEQ ID NO: 43, 44 |

TABLE 3 -continued

| Recombinant synthase | Nucleic acid substitution | Amino acid substitution | Primers |
|---|---|---|---|
| pPs619C1309 | GAA → GAT | E130D | SEQ ID NO: 15, 16 |
| | AGC → CAT | S477H | SEQ ID NO: 33, 34 |
| | CAG → CGC | Q481R | SEQ ID NO: 45, 46 |
| pPs619C1310 | GAA → GAT | E130D | SEQ ID NO: 15, 16 |
| | AGC → TTT | S477F | SEQ ID NO: 35, 36 |
| | CAG → AAA | Q481K | SEQ ID NO: 41, 42 |

TABLE 4

| Recombinant synthase | Nucleic acid substitution | Amino acid substitution | Primers |
|---|---|---|---|
| pPs619C1311 | GAA → GAT | E130D | SEQ ID NO: 15, 16 |
| | AGC → TTT | S477F | SEQ ID NO: 35, 36 |
| | CAG → ATG | Q481M | SEQ ID NO: 43, 44 |
| pPs619C1312 | GAA → GAT | E130D | SEQ ID NO: 15, 16 |
| | AGC → TTT | S477F | SEQ ID NO: 35, 36 |
| | CAG → CGC | Q481R | SEQ ID NO: 45, 46 |
| pPs619C1313 | GAA → GAT | E130D | SEQ ID NO: 15, 16 |
| | AGC → TAT | S477Y | SEQ ID NO: 37, 38 |
| | CAG → AAA | Q481K | SEQ ID NO: 41, 42 |
| pPs619C1314 | GAA → GAT | E130D | SEQ ID NO: 15, 16 |
| | AGC → TAT | S477Y | SEQ ID NO: 37, 38 |
| | CAG → ATG | Q481M | SEQ ID NO: 43, 44 |
| pPs619C1315 | GAA → GAT | E130D | SEQ ID NO: 15, 16 |
| | AGC → TAT | S477Y | SEQ ID NO: 37, 38 |
| | CAG → CGC | Q481R | SEQ ID NO: 45, 46 |

TABLE 5

| Recombinant synthase | Nucleic acid substitution | Amino acid substitution | Primers |
|---|---|---|---|
| pPs619C1400 | GAA → GAT | E130D | SEQ ID NO: 15, 16 |
| | AGC → ACC | S325T | SEQ ID NO: 17, 18 |
| | AGC → CGC | S477R | SEQ ID NO: 31, 32 |
| | CAG → ATG | Q481M | SEQ ID NO: 43, 44 |
| pPs619C1401 | GAA → GAT | E130D | SEQ ID NO: 15, 16 |
| | AGC → ACC | S325T | SEQ ID NO: 17, 18 |
| | AGC → CGC | S477R | SEQ ID NO: 31, 32 |
| | CAG → AAA | Q481K | SEQ ID NO: 41, 42 |
| pPs619C1334 | GAA → GAT | E130D | SEQ ID NO: 15, 16 |
| | AGC → ACC | S325T | SEQ ID NO: 17, 18 |
| | AGC → TTT | S477F | SEQ ID NO: 35, 36 |
| | GAG → ATG | Q481M | SEQ ID NO: 43, 44 |
| pPs619G1336 | GAA → GAT | E130D | SEQ ID NO: 15, 16 |
| | AGC → ACC | S325T | SEQ ID NO: 17, 18 |
| | AGC → GGC | S477G | SEQ ID NO: 39, 40 |
| | CAG → ATG | Q481M | SEQ ID NO: 43, 44 |
| pPs619C1339 | GAA → GAT | E130D | SEQ ID NO: 15, 16 |
| | AGC → ACC | S325T | SEQ ID NO: 17, 18 |
| | AGC → TTT | S477F | SEQ ID NO: 35, 36 |
| | CAG → AAA | Q481K | SEQ ID NO: 41, 42 |

INDUSTRIAL APPLICABILITY

As described and proven above, the present invention provides a copolymer comprising 4-hydroxybutyrate monomer unit and lactate monomer unit or a copolymer 4-hydroxybutyrate monomer unit, lactate monomer unit and 3-hydroxyalkanoate. The present invention also provides a method for preparing the copolymer, wherein the method comprises culturing a cell or plant comprising the gene of enzyme converting lactate and 3-hydroxyalkanoate into lactyl-CoA and 3-hydroxyalkanoyl-CoA, respectively, phosphotransbutylase gene, butyrate kinase gene and polyhydroxyalkanoate (PHA) synthase gene together. The copolymer of the present invention is a biodegradable polymer being able to be usefully used instead of conventional synthetic plastic, and the copolymer can be used for medical use.

---

What is claimed is:

1. A method for preparing a copolymer comprising at least one lactate monomer unit and at least one 4-hydroxybutyrate monomer unit,
   wherein the method comprises culturing a cell or a plant comprising
   (a) a gene encoding an enzyme that converts lactate and 3-hydroxyalkanoate into lactyl-CoA and 3-hydroxyalkanoyl-CoA, respectively,
   (b) a phosphotransbutylase gene,
   (c) a butyrate kinase gene and
   (d) a polyhydroxyalkanoate (PHA) synthase gene.

2. The method of claim 1,
   wherein the cell or the plant is obtained
   by transforming a cell or a plant not having at least one among the (a), (b), (c) and (d) genes with the gene(s) that the cell or the plant does not have among the (a), (b), (c) and (d) genes.

3. The method of claim 1,
   wherein the gene encoding the enzyme that converts lactate and 3-hydroxyalkanoate into lactyl-CoA and 3-hydroxyalkanoyl-CoA, respectively, is the propionyl-CoA transferase gene (pct).

4. The method of claim 1,
   wherein the phosphotransbutylase gene is isolated from *Clostridium acetobutyricum*.

5. The method of claim 1,
   wherein the butyrate kinase gene is isolated from *Clostridium acetobutyricum*.

6. The method of claim 1,
   wherein the polyhydroxyalkanoate (PHA) synthase gene is phaC1$_{Ps6-19}$ isolated from *Pseudomonas* sp. 6-19.

7. The method of claim 1,
   wherein the PHA synthase gene encodes the amino acid sequence of SEQ ID NO: 8 having mutations of
   a) S325T and Q481M;
   b) E130D and Q481K;
   c) S325T and Q481K;
   d) E130D and Q481M;
   e) E130D and Q481R;
   f) E130D, S325T and Q481M;
   g) E130D, S325T and Q481K;
   h) E130D, S477R and Q481K;
   i) E130D, S477R and Q481M;
   j) E130D, S477R and Q481R;
   k) E130D, S477H and Q481K;
   l) E130D, S477H and Q481M;
   m) E130D, S477H and Q481R;
   n) E130D, S477F and Q481K;
   o) E130D, S477F and Q481M;
   p) E130D, S477F and Q481R;
   q) E130D, S477Y and Q481K;
   r) E130D, S477Y and Q481M;
   s) E130D, S477Y and Q481R;
   t) E130D, S325T, S477R and Q481M;
   u) E130D, S325T, S477R and Q481K;
   v) E130D, S325T, S477F and Q481M;
   w) E130D, S325T, S477G and Q481M; or
   x) E130D, S325T, S477F and Q481K.

8. The method of claim 1,
   wherein the cell is a microorganism.

9. The method of claim 8,
   wherein the microorganism is *E. coli*.

10. The method of claim 1,
    wherein the culturing is performed in a medium comprising at least one selected from the group consisting of 4-hydroxybutyrate, 3-hydroxypropionate and 3-hydroxybutyrate.

11. A method for preparing a copolymer comprising recurring lactate monomer units and 4-hydroxybutyrate monomer units,
    wherein the method comprises culturing a cell or a plant comprising the gene encoding an enzyme that converts lactate and 3-hydroxyalkanoate into lactyl-CoA and 3-hydroxyalkanoyl-CoA, respectively,
    the Cat2 gene encoding an enzyme that converts 4-hydroxybutyrate into 4-hydroxybutyryl-CoA; and
    the PHA synthase gene.

12. The method of claim 11,
    wherein the Cat2 gene is isolated from *Clostridium kluyveri* and has the nucleotide sequence of SEQ ID NO: 30.

* * * * *